United States Patent [19]
Christensen et al.

[11] Patent Number: 5,713,960
[45] Date of Patent: Feb. 3, 1998

[54] PROSTHESIS WITH IMPROVED BIOCOMPATIBILITY MADE WITH N-VINYL POLYMERS

[76] Inventors: James Marlow Christensen, 520 S. Vermont Ave., Glendora, Calif. 91740; Parviz Robert Ainpour, 3744 Ramsdale, La Crescenta, Calif. 91214

[21] Appl. No.: 734,407

[22] Filed: Oct. 16, 1996

Related U.S. Application Data

[63] Continuation of Ser. No. 302,782, filed as PCT/US92/02259, Mar. 19, 1992, published as WO93/00867, Jan. 21, 1993, abandoned, which is a continuation-in-part of Ser. No. 549,096, Jul. 6, 1991, Pat. No. 5,116,371.

[51] Int. Cl.$^6$ .......................................................... A61F 2/02
[52] U.S. Cl. ........................... 623/11; 623/8; 623/4; 623/15; 523/113; 523/115
[58] Field of Search ............................. 623/4, 8, 11, 15, 623/1; 523/113, 115

[56] References Cited

U.S. PATENT DOCUMENTS

| | | | |
|---|---|---|---|
| 4,026,296 | 5/1977 | Stoy et al. | 128/207.15 |
| 4,138,382 | 2/1979 | Polmanteer | 260/29.6 |
| 4,189,546 | 2/1980 | Deichert et al. | 623/6 |
| 4,228,269 | 10/1980 | Loshaek et al. | 526/346 |
| 4,517,326 | 5/1985 | Cordts et al. | 524/310 |
| 4,648,880 | 3/1987 | Brauman | 623/8 |
| 4,734,475 | 3/1988 | Goldenberg et al. | 526/273 |
| 4,790,848 | 12/1988 | Cronin | 623/8 |
| 5,007,940 | 4/1991 | Berg | 623/8 |
| 5,116,371 | 5/1992 | Christensen et al. | 623/11 |
| 5,116,387 | 5/1992 | Berg | 623/66 |
| 5,273,750 | 12/1993 | Homiger et al. | 623/6 |

*Primary Examiner*—Paul B. Prebilic
*Attorney, Agent, or Firm*—Michael J. Ram; Marvin H. Kleinberg; Marshall A. Lerner

[57] ABSTRACT

An injectable or implantable material for soft tissue augmentation comprising a hydrogel containing both hydrophobic and hydrophilic domains is prepared by copolymerizing a hydrophilic monomer, such as water soluble N-vinylpyrrolidone with non-water soluble monomers, such as N-vinyl carbazole, its derivatives, or a non-water soluble derivative of N-vinylpyrrolidone. Also suitable for injection into direct contact with body tissue are hydrogels prepared by cross-linking polyvinylpyrrolidone. The hydrogel may be either solid or composed of particles. The hydrogel may also be enclosed within a flexible porous or nonporous envelope.

23 Claims, No Drawings

PROSTHESIS WITH IMPROVED BIOCOMPATIBILITY MADE WITH N-VINYL POLYMERS

This is a continuation of application Ser. No. 08/302,782, filed Sep. 12, 1994 and now abandoned, which is a national state 371 filing in the U.S. of PCT/US92/02259 filed Mar. 19, 1992, which is a continuation-in-part of Ser. No. 07/549,096, filed Jul. 6, 1991 now U.S. Pat. No. 5,116,371.

BACKGROUND

The present invention relates to improved implantable prostheses, compositions and methods used to reconstruct soft tissue. More particularly, the invention relates to soft tissue prostheses combining a hydrogel within an envelope in order to minimize capsular formation and contracture, and injectable or implantable hydrogel materials for augmenting or replacing soft tissue in mammals.

Reconstruction of soft tissues using a silicone elastomer bag filled with silicone gel is a common surgical procedure. Additionally, soft tissue has been reconstructed or augmented by using autografts and homografts of bone, cartilage, fatty tissue or dermis, the insertion of alloplastic implants, or the injection of alloplastic materials, such as liquid silicone collagen, or body compatible polymers solution. All of these materials have undesirable side effects. However, they are used because better alternatives are not available.

An implant composed of a silicone elastomer bag filled with a silicone gel was described by Cronin in U.S. Pat. No. 3,293,663 for reconstruction of the human breast. However, after a short period of time a capsule composed of fibrous scar tissue forms around the implant. It is commonly believed that silicone gel "bleeding" through the bag causes an inflammatory response which results in this capsular formation. Thickening and eventual contracture of the fibrous capsule results in hardening and spherical deformation of the implant and surrounding tissues. The implant becomes painful, aesthetically unacceptable and can cause erosion of the overlying tissues.

The use of saline filled silicone elastomer bags and double-lumen implants with the outer chamber containing saline, decreases the inflammatory response. However, failure of the silicone elastomer bag, especially along folds, is more common with saline filled implants. This is due to abrasion of the bag against itself, frequent flexing of the material as the patient moves, the low viscosity of the filling material, and the decreased lubricity of the saline compared to silicone gel. Rupture of a saline filled implant allows the tissue cavity to shrink as the saline is absorbed into the surrounding tissues.

U.S. Pat. No. 4,157,085 to Austad discloses hydrophilic polymers, such as poly-N-vinylpyrrolidone, carboxymethylcellulose, or polyethylene glycol encapsulated within a membrane permeable to extracellular body fluids under osmotic pressure. The preferred material is a very thin silicone membrane capable of transmitting fluids as well as stretching as the fluid concentration of the enclosed material increases. This device is intended to be used to stretch tissue as the polymer inside the envelope absorbs fluid. When tissue expansion is completed, the device is removed and replaced with a suitable prosthesis. This is necessary since the polymers inside the envelope are water soluble, not cross-linked, and would readily disperse in the body if they should escape from the device if its membrane ruptured or tore.

Polmanteer in U.S. Pat. No. 4,138,382 discusses the use of hydrophilic gels which are copolymers of olefinic hydrolyzable silanes and water soluble vinylic constituents. These gels swell in the presence of water to form a loose cross-linked network using siloxane [≡S—O—Si≡] as the covalent cross-linking entity. However, this results in a gel which can dissociate in water according to the equilibrium reaction

and become soluble. Such gels would slowly be absorbed into the tissue in the event of a rupture or tear in the envelope.

U.S. Pat. No. 4,517,326 to Cordts suggests the use of a polyurethane gel containing an aqueous dispersion for use as an implantable prosthesis. The water level in the gel can only be varied from 25% to 65% which limits the softness of the device. Additionally, such a device would contain macroporosity in the form of dispersed water droplets and be susceptible to calcification and tissue in-growth.

Bone and cartilage can be used to fill a soft tissue defect, but unless the depressed area is due to a deficiency of underlying bony framework, the lack of pliability in the augmented area will be unsatisfactory. The surgical technique of inserting bone, cartilage or dermis often involves wide undermining of soft tissue and the creation of a substantial, and sometimes additional, recipient site scar. There is also a tendency for such grafts to undergo resorption which often cannot be predicted accurately. Moreover, fine contouring of multiple small areas is often extremely difficult with such grafts. The donor sites for obtaining bone and cartilage autografts are rather limited and a noticeable scar is often created at the donor site.

The donor site problems are not existent with the use of homograft material. However, homograft dermis is unsuitable because it is always rejected. Rejection may be less of a problem with bone and cartilage homografts, but the results are unpredictable.

Implantation of alloplastic materials, such as solid silicone elastomer, require that the recipient site be undermined resulting in a scar at the insertion site. These materials have a significant tendency to drift, cause seromas, become surrounded by hard fibrous tissue and occasionally become infected or erode through the overlying soft tissue.

Injection of alloplastic materials, such as silicone liquids and gels reduce the surgery involved and the resulting scar formation. However, it has been found that silicone liquids and gels are not immobilized by the tissue and tend to migrate out of the intended recipient site and eventually collect in the lymph nodes. Auto-immune disease, hard fibrous encapsulation, and deformation of the reconstruction or augmentation has been reported from the use of these materials both from direct injections and when contained in a silicone bag typically used in breast implants.

Soluble collagen has been used as a subcutaneous implant for repairing dermatological defects, such as scars, furrows, and other soft tissue defects. Collagen can be injected directly into the recipient site thereby minimizing scar formation. Although it appears that this material is readily accepted, the repair of the defects is temporary as the collagen or collagen based materials can be enzymatically decomposed by the body, i.e., by the action of collagenase, and patients need the treatment repeated after 6 to 18 months. There have also been a number of adverse tissue responses after utilization of soluble collagen.

Various medical researchers have evaluated the implantation of hydrogel as a breast tissue replacement or a tissue replacement material. The hydrogel used primarily has been poly(hydroxyethyl-methacrylate) (pHEMA). Depending on the water content, cross-linking agent, monomer content, and pore structure as well as other variables within these hydrogels or implant structures a broad range of tissue interaction have been reported. These interactions include encapsulation, small and giant cell growth, vascularization and calcification. In general, pHEMA hydrogels with high water contents exhibit poorer mechanical properties, vascularization, tend to calcify, are difficult to shape, and are readily damaged during implantation due to their fragility. This tissue response is believed to be due to their macroporous structure at high water contents. Lower water content pHEMA hydrogels which are homogeneous, or have only microporosity, do not exhibit vascularization or calcification. However, they are generally stiffer and less malleable making them unsuitable for soft tissue augmentation and have a greater tendency to incite a fibrous capsule.

U.S. Pat. No. 4,631,188 to Stoy, et al. discloses non-water soluble hydrogels dissolved in a water-soluble solvent for injection into soft tissue. As the solvent is absorbed by the body it is partially replaced by water forming a semi-rigid aquagel.

The prior art also discloses viscous materials implanted in the body which have been referred to as hydrogels. However, these materials are not true hydrogels as they are polymers dissolved in water and, thus, they expand infinitely on addition of more solvent; or, they form gels at certain temperatures and solutions at different temperatures, this conversion being reversible; or, water is not in equilibrium with the polymer as is the case in true hydrogels.

Thus, for the successful post-mastectomy reconstruction, as well as other procedures involving implants of a soft tissue prosthesis, there is a need for a prosthesis which is soft and malleable, does not calcify or incite severe fibrous encapsulation, and is resistant to leakage in the event of envelope rupture or tear. There is also a need for an implantable material which is soft and malleable, does not calcify or incite unacceptable fibrous encapsulation, and can be implanted or delivered into the site either as a shaped mass or by injection, through a small gauge needle.

SUMMARY

According to the present invention these needs are met by an improved implantable prostheses for use in the human body comprising a flexible envelope that contains within it a soft, malleable biocompatible hydrogel filling containing both hydrophobic and hydrophilic domains. The envelope, formed from either a flexible porous or non-porous material, may be single or multi-lumen. The construction designs provide long term stability even in the event of envelope tear or rupture.

The hydrogel of the invention has a discrete dimension; i.e., is not infinitely expandable, and, when mixed with a physiological solution, forms a non-reversible gel having a defined water content, the gel not being enzymatically decomposed by the body. The resultant hydrogel is homogeneous, biocompatible and relatively non-reactive with the body. The hydrogel can be cross-linked polyvinyl pyrrolidone, polymerized N-vinylic monomers, hydrolyzed polyacrylonitriles, or combinations thereof.

Instead of being placed in an envelope, the gel can be implanted as a shaped mass or it can be injected into the desired location in particulate form. Further, the hydrogel can be implanted or injected either fully hydrated, partially hydrated or in a dehydrated form to replace or augment body fluid or body tissue, or to reconstruct body tissue. Thus, hydrogels embodying features of the invention can be used to replace soft body parts surgically removed or depleted as a result of age or use, to reconstruct soft tissue damaged by external causes, to augment body parts, such as for subcutaneous dermatological use, breast enlargement, and other common plastic surgery, procedures or to replace body fluids, such as synovial fluid or vitreous or aqueous fluid in the eye.

DESCRIPTION

Hydrogels embodying features of the invention are made by copolymerization of N-vinylpyrrolidone with a multifunctional cross-linker or by copolymerization of a hydrophobic monomer with a hydrophilic monomer. A small amount of multi-functional monomer can also be used as a covalent cross-linker to produce a thermoset copolymer which is insoluble in both aqueous and organic media. Even in the absence of a covalent cross-linking monomer, hydrogels, in an aqueous environment, will remain as a gel due to interaction of the hydrophobic domains. The interactions caused by hydrophobic, ionic, dipolar, hydrogen bonding or a combination of these forces results in a hydrogel in which the polymer chains are "cross-linked" through the hydrophobic domains. In aqueous solutions, these hydrogels will swell and hold water uniformly in the hydrophilic domains of the polymer without any macroporosity or heterogeneity. This homogeneity reduces or prevents calcification. The hydrophobic domains which are uniformly spread throughout the matrix of the gel hold the polymer chains together and do not allow them to dissolve and dissipate into body fluids.

The water content of the hydrogel, which typically varies from 40% to 99%, is controlled by the ratio of hydrophobic to hydrophilic domains. Hydrogels having water contents over 85% will generally be similar in texture to soft tissue, have sufficient strength to allow handling and implantation, and have a homogeneous microporous structure to prevent vascularization and calcification. These hydrogels can be passed through a needle as small as 30 gauge.

Suitable hydrophilic monomers that can be used to form the gel are biocompatible, water soluble vinylic compounds. The term "vinylic" means a compound or constituent containing at least one unsaturated aliphatic linkage in the form of $CH_2$=$CRR'$. Included in the class of hydrophilic monomers are N-vinylpyrrolidone, acrylates or methacrylates having the general formula

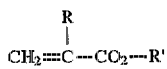

where R is H or $CH_3$ and R' are radicals derived from monohydric or dihydric alcohols such as $CH_2$—$CH_2$—OH or $CH_2$—$CH(CH_3)$—OH or $CH_2$—$CH(OH)$—$CH_2$—OH or monomers having the general formula

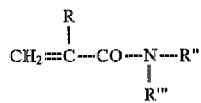

wherein R is H or $CH_3$ and R" and R'" can be H, alkyl, or alkane derived radicals, such as $CH_3$—,$C_2H_5$— or monohydric alcohols, such as $CH_2$—$CH(OH)$—$CH_3$ Other vinylic constituents containing 2 or more vinylic groups can be used to modify the properties, such as the swelling, solubility, flexibility and cohesiveness of the gel.

Suitable hydrophobic monomers that can be reacted with the hydrophilic monomers are biocompatible, hydrophobic vinylic compounds. Included in the class of hydrophobic monomers are acrylates, methacrylates and $RR'$—N—$CH_2$=$CH_2$. Examples include monomers having the following general formula

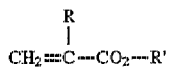

where R is H or $CH_3$ and R' is $CH_3$, $CH_2$—$CH_3$ or higher alkyls, benzyl, phenyl or other suitable aromatic groups.

Other suitable hydrophobic monomers include non-water soluble derivatives of N-vinylpyrrolidone, or aromatic derivatives of N-vinylpyrrolidone. The term aromatic derivatives of N-vinylpyrrolidone refers to N-vinylpyrrolidone with one or more aromatic rings attached thereto, such as N-vinyl carbazole. These derivatives may also include pendant groups, such as oxygen, halogen or alkyls.

A material particularly suited for injection is polyvinyl pyrrolidone which has been copolymerized by the addition of diethylene glycol dimethylacrylate (DEGDMA). This creates a non-reversible covalently cross-linked hydrogel of known water up take and swelling characteristics.

Other classes of hydrogels having both hydrophobic and hydrophilic domains which are suitable for placement directly in contact with tissue include polyurethanes containing a hydrophilic polyol domain and a hydrophobic alky or aryl di-isocyanate. Similarly, hydrogels can be formed from hydrolyzed poly-acrylonitriles containing carboxylic acid or amide groups that form the hydrophilic domains, and nitrile [—C≡N] groups that interact strongly to form the hydrophobic domains.

The envelope containing the hydrogel may be formed from any suitable material that is flexible and biocompatible. Non-porous materials, such as silicone or polyurethane having either a smooth or textured surface may be used. Porous materials made from fabricated polymers which are woven, knitted, felted or veloured, or materials which are foamed, stretched, or expanded may also be used. The pore size of these materials should be less than the smallest particle size of hydrogel used to fill the prosthesis in order to avoid loss of hydrogel from the envelope. Permeable membranes, such as thin cellulosic or silicone may also be used.

EXAMPLE 1

A single walled silicone elastomer bag is filled with hydrogel then sealed to provide a barrier to fluid and tissue exchange. The hydrogel inside the bag is a solid mass preferably having a shape similar to the desired natural contour of the body. Such a hydrogel would preferably have a high water content around 95% to 99% in order to provide the desired softness to the implant. However, a lower water content hydrogel could be used if a stiffer implant was desired.

Likewise, the hydrogel inside the bag could be composed of many pieces ranging from chunks down to very small particles. The water content of the hydrogel would depend on the size of the particle and the desired softness of the implant. Large particle sizes would preferably use high water content hydrogels around 95% to 99%, similar to the solid mass described above. Smaller particle sizes could use lower water content hydrogels down to 40% to achieve the same effect due to the fluidity of the particles. If higher water content hydrogels were used with small particles a more "gelatinous" type structure would be obtained.

EXAMPLE 2

A single walled bag formed from a porous material is filled with hydrogel then closed to prevent escape of the hydrogel. Suitable materials for the bag would be biocompatible, would not elicit a severe foreign body response, and would have a pore size less than the particle size of the hydrogel. Preferred material would be fabrics made from Teflon, Dacron or other biocompatible polymers which may be woven, knitted, braided, or formed into felt, or velour. Other preferred materials would include permeable membranes or expanded material, such as Teflon which are made porous by stretching. Such a material is sold commercially under the name Goretex.

As in Example 1 discussed above, the hydrogel inside the porous bag could be of several forms and water contents depending on the desired natural curvature and stiffness desired. In this example body fluids are able to transport through the porous bag so that the fluid content inside the bag will stay in equilibrium with the surrounding tissue. However, the components of the hydrogel are retained within the envelope. Tissue in-growth, if desired, is regulated by the envelope construction and pore size.

EXAMPLE 3

A double lumen implant can be constructed from a bag within a bag. The inner wall and contents of the inner bag can be formed from any materials known to the art. This would include, for example, silicone gel contained within a silicone elastomer bag. The inner lumen can also be formed according to the present invention as discussed in Examples 1 and 2 above.

The outer lumen is formed with hydrogel surrounding the inner wall and contained within the outer bag. The hydrogel and flexible outer bag can be formed as described in Examples 1 and 2 above.

EXAMPLE 4

A multiple lumen implant can be formed similar to that described in Example 3. For a multiple lumen implant all of the inner walls can be formed with any material known to the art or encompassed in the present invention. The outer wall or walls are formed according to the present invention as discussed in Examples 1 and 2.

EXAMPLE 5

Various different compositions can be prepared which are suitable for surgical implantation without an enclosing bag structure or which can be injected directly into the body as a tissue replacement. For example, 80% N-vinylpyrrolidone, 10% N-vinylphthalamid and 1% DEGDMA was polymerized to produce a hydrogel containing 90% by weight water. This hydrogel had the consistency of soft tissue, was easily formed into a desired permanent shape, and was easy to handle and insert into the body during surgery.

EXAMPLE 6

A hydrogel with a 95% water content was formed by copolymerizing 90% N-vinylpyrrolidone with 10% N-vinylphthalamid. After hydrating this material was readily injected into a body tissue site through a cannula as small as 30 gauge.

EXAMPLE 7

In another variation, a powder was formed from the dehydrated hydrogel of Example 6. Prior to use, the powder was mixed with a physiological solution to form a hydrogel powder suspension. This suspension was injected into soft tissue at the site to be augmented. After injection, the hydrogel powder absorbed body fluids and swelled causing the tissue to be expanded at the augmentation site.

Because, the hydrogels of the invention have a fixed water content when hydrated and, thus, a known amount of swelling when exposed to body fluids, structures with dimensions smaller than in the hydrated state can be formed in a dry state and these reduced size structures can be implanted surgically, through a suitable sized cannula, or through minimally invasive surgical devices, such as a laparoscope. As an example, the hydrogel from Example 5 was formed in a dry state into a geometry which would result in the desired shape and dimensions when fully hydrated.

In a second variation, the dry hydrogel from Example 6 was formed into a cylindrical shape 3 mm in diameter and the cylinder was passed through the tube of an instrument into a body cavity where it expanded to approximately 10 mm in diameter after hydration.

Although the invention has been described with reference to certain preferred variations and uses thereof, other variations and uses are possible without departing from its intended scope. Thus, for example, in addition to mammary prosthesis the improved implantable devices of this invention can also be prepared in different shapes and forms for the purpose of supplementing, augmenting or replacing tissue anywhere on or in the animal or human body for aesthetic, reconstructive medical purposes. Augmentation of tissue include augmentation of hypoplastic or missing tissue for reconstructive purposes. Additionally, the hydrogel can be prepared in different shapes or particle sizes and injected or implanted for the purpose of supplementing, augmenting or replacing tissue or body fluids anywhere on or in the animal or human body for aesthetic or reconstructive purposes.

What is claimed:

1. A hydrogel for placement in contact with body tissue within a mammalian body to replace or augment tissue or body fluids:
    said hydrogel consisting of N-vinyl pyrrolidone and an N-vinylic hydrophobic monomer reacted to form a polymer having hydrophilic and hydrophobic domains.

2. The hydrogel of claim 1 wherein the hydrophobic domains of the hydrogel are held together with hydrophobic bonding, ionic bonding, dipolar bonding, hydrogen bonding or a combination of these forces.

3. The hydrogel of claim 1 wherein the hydrogel is prepared by the copolymerization of a hydrophilic monomer with an N-vinylic hydrophobic monomer.

4. The hydrogel of claim 1 wherein the water concentration of the fully hydrated hydrogel is from about 40% by weight to about 99% by weight.

5. The hydrogel of claim 1 wherein the water concentration of the fully hydrated hydrogel is greater than about 85% by weight.

6. The hydrogel of claim 4 wherein the hydrogel can be passed through a 30 gauge needle.

7. The hydrogel of claim 1 wherein the hydrogel is suspended in a physiological solution for placement in a mammalian body.

8. The method of reconstructing or augmenting the tissue of a mammalian body comprising the placement of a hydrogel polymer in contact with body tissue,
    said hydrogel consisting of N-vinyl pyrrolidone and an N-vinylic hydrophobic monomer reacted to form a polymer having hydrophilic and hydrophobic domains, the hydrogel polymer when fully hydrated capable of filling a space within the body tissue.

9. The process of claim 8 wherein the hydrogel is mixed with a sufficient quantity of an aqueous solution to fully hydrate the hydrogel.

10. The process of claim 9 wherein the fully hydrated polymer is placed in the desired location in the body by passing it through a tubular device inserted into the body.

11. The process of claim 9 wherein the fully hydrated polymer is shaped into a desired form and the desired form is surgically inserted into the body.

12. The process of claim 8 wherein the hydrogel is placed in the body in a less than fully hydrated state.

13. The process of claim 12 wherein the hydrogel is dehydrated before placement in the body.

14. The process of claim 13 wherein the hydrogel is formed into a shape such that when fully hydrated the hydrogel will expand to a desired final dimension.

15. The process of claim 13 wherein the hydrogel is powdered, dispersed in a physiological solution and placed into the body through a tubular device inserted into the body.

16. The process of claim 13 wherein the hydrogel is formed into a shape and placed into the body through a tubular device inserted into the body.

17. A hydrogel for placement in contact with body tissue within a mammalian body to replace or augment tissue or body fluids:
    said hydrogel consisting of a polymer having hydrophilic and hydrophobic domains,
    the hydrophilic domain being derived from a water soluble monomer of N-vinylpyrrolidone or a vinylic compound of the formula

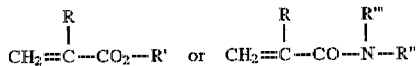

wherein R is H or $CH_3$ R' is $CH_2$—$CH_2$—OH, $CH_2$—$CH(CH_3)$—OH or $CH_3$—$CH(OH)$—$CH_2$—OH and R" and R''' are H, $CH_3C_2H_5$ or $CH_2$—$CH(OH)$—$CH_3$
    the hydrophobic domain
    a) being derived from a non-water soluble monomer of the formula

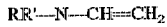

where R is H or $CH_3$ and R' is $CH_3$, $CH_2$—$CH_3$ or higher alkyls, or an aromatic group or
    b) is selected from the group consisting of N-vinyl carbazole, N-vinylphthalimide and its derivatives, non-water soluble derivatives of N-vinylpyrrolidone, and aromatic derivatives of N-vinylpyrrolidone.

18. The hydrogel of claim 17 wherein the hydrophobic monomer is selected from the group consisting of N-vinyl carbazole, derivatives of N-vinyl carbazole, non-water soluble derivatives of N-vinylpyrrolidone and aromatic derivatives of N-vinylpyrrolidone.

19. The hydrogel of claim 18 wherein the derivative of N-vinyl carbazole, the non-water soluble derivatives of N-vinylpyrrolidone and aromatic derivatives of N-vinyl pyrrolidone includes a pendant group selected from the group consisting of oxygen, halogen, and alkyls.

20. The hydrogel of claim 17 wherein the water concentration of the fully hydrated hydrogel is from about 40% by weight to about 99% by weight.

21. The hydrogel of claim 17 wherein the water concentration of the fully hydrated hydrogel is greater than about 85% by weight.

22. The hydrogel of claim 17 wherein the hydrogel can be passed through a 30 gauge needle.

23. The hydrogel of claim 21 wherein the hydrogel is suspended in a physiological solution for placement in a mammalian body.

* * * * *